United States Patent
Yeager

(10) Patent No.: US 7,955,333 B2
(45) Date of Patent: Jun. 7, 2011

(54) METHOD OF PREPARING A PATIENT'S LEG IN NEED OF TREATMENT, FOR AMBULATION

(76) Inventor: David A. Yeager, Dixon, IL (US)

(*) Notice: Subject to any disclaimer, the term of this patent is extended or adjusted under 35 U.S.C. 154(b) by 214 days.

(21) Appl. No.: 11/985,549

(22) Filed: Nov. 15, 2007

(65) Prior Publication Data

US 2009/0131935 A1 May 21, 2009

(51) Int. Cl.
*A61F 5/052* (2006.01)

(52) U.S. Cl. ............................. 606/56; 606/54

(58) Field of Classification Search .............. 606/53–59, 606/279
See application file for complete search history.

(56) References Cited

U.S. PATENT DOCUMENTS

| | | | |
|---|---|---|---|
| 4,338,927 A * | 7/1982 | Volkov et al. ................ 606/56 |
| 4,721,101 A * | 1/1988 | Gardner et al. ............... 601/152 |
| RE32,940 E * | 6/1989 | Gardner et al. ............... 601/152 |
| 4,998,935 A | 3/1991 | Pennig | |
| 5,020,523 A * | 6/1991 | Bodine .......................... 602/27 |
| 5,088,478 A | 2/1992 | Grim | |
| 5,281,221 A * | 1/1994 | Tadych ........................... 606/53 |
| 5,399,152 A * | 3/1995 | Habermeyer et al. .......... 602/23 |
| 5,429,588 A * | 7/1995 | Young et al. .................... 602/27 |
| 5,448,790 A * | 9/1995 | Saro et al. ........................ 5/657 |
| 5,520,627 A * | 5/1996 | Malewicz ....................... 602/26 |
| 5,584,798 A * | 12/1996 | Fox ............................... 601/152 |
| 5,931,837 A * | 8/1999 | Marsh et al. .................... 606/55 |
| 5,944,678 A * | 8/1999 | Hubbard ........................ 602/27 |
| 6,485,447 B1 | 11/2002 | Lavery et al. | |
| 6,514,254 B1 * | 2/2003 | Falls ............................... 606/54 |
| 6,551,280 B1 * | 4/2003 | Knighton et al. ............. 604/133 |
| 6,918,197 B2 | 7/2005 | Ellis | |
| 2002/0130538 A1 * | 9/2002 | Artsvelyan .................... 297/227 |
| 2003/0009167 A1 * | 1/2003 | Wozencroft ..................... 606/55 |
| 2003/0125653 A1 * | 7/2003 | Meyer ............................ 602/27 |
| 2004/0064078 A1 * | 4/2004 | Winters .......................... 602/27 |
| 2004/0097923 A1 * | 5/2004 | Shevlin ........................... 606/54 |
| 2004/0138659 A1 * | 7/2004 | Austin et al. .................... 606/54 |
| 2005/0059968 A1 * | 3/2005 | Grant et al. ..................... 606/54 |
| 2005/0101887 A1 | 5/2005 | Stark et al. | |
| 2005/0159690 A1 * | 7/2005 | Barak et al. ................... 601/149 |
| 2006/0079822 A1 * | 4/2006 | Hjorth ............................ 602/28 |
| 2007/0161983 A1 * | 7/2007 | Cresina et al. .................. 606/54 |
| 2008/0132817 A1 * | 6/2008 | Vito ............................... 602/23 |

* cited by examiner

*Primary Examiner* — Eduardo C Robert
*Assistant Examiner* — Jerry Cumberledge
(74) *Attorney, Agent, or Firm* — Wood, Phillips, Katz, Clark & Mortimer

(57) ABSTRACT

A method of preparing a patient's one leg, that is in need of treatment, for ambulation. The method includes the steps of: applying an external fixation assembly, having at least one external frame component, by pinning the at least one external frame component to at least one of the patient's bones in the patient's one leg so as to prepare the patient's one leg for healing; providing a foot assembly with a sole assembly defining a bearing surface and a connecting assembly; and operatively joining the foot assembly to the patient's one leg, whereby the patient can walk in a manner whereupon weight of the patient's body is applied by a patient's one foot, that is part of the user's one leg, to the sole assembly and therethrough to and against an underlying surface during ambulation.

24 Claims, 5 Drawing Sheets

METHOD OF PREPARING A PATIENT'S LEG IN NEED OF TREATMENT, FOR AMBULATION

BACKGROUND OF THE INVENTION

1. Field of the Invention

This invention relates to a method of preparing a patient's leg, to which an external fixation assembly is applied to prepare the patient's leg for healing, for ambulation through the use of a foot assembly.

2. Background Art

External fixation is a process used to facilitate healing of certain types of bone fractures and treat various foot and ankle pathologies.

One form of external fixation utilizes an external fixation assembly, consisting of plural frame components that are operatively interconnected. Pins, screws, and/or cables extend from the frame components through a patient's soft tissue and into his/her bones to effect setting at a fracture site and/or immobilize or strategically orient the foot to promote healing thereof.

Once the external fixation assembly is put in place on a patient's leg, it is generally preferred that the patient engage in weight bearing activity that has proven to stimulate circulation and promote healing. For example, ambulation causes micromotion at a fracture site that advances healing.

Heretofore, it has been common to wrap the patient's foot, as with several layers of a heavy cloth, typically of a type used to form towels, that are held in place as by an outer retaining wrap. During ambulation, the patient applies his/her weight to a cushioning accumulation of cloth in the wrap that does not have a bearing surface of consistent shape or resiliency. As a result, during ambulation, the bearing forces may be unpredictably transmitted, potentially in a detrimental manner through the patient's leg. This may cause patients to avoid prescribed regular ambulation.

The patient may also be unstable in bearing his/her weight upon the wrap, potentially leading to a detrimental twisting of the body, or worse yet, a fall. Adaptation on the user's part to this type of wrap may lead to muscular compensation that introduces other complications that may develop over a typical six to twelve week recovery period. Whereas, ideally the physician would be able to prepare the patient to ambulate consistently in a manner that optimizes healing, this is not possible with the above practice, or utilizing known alternatives.

A further problem with the above wrapping procedure is that it may be difficult or impossible to effect wrapping in a manner whereby the patient is consistently comfortable and healing is promoted. The initial wrapping procedure is generally carried out at a physician's office. As the patient ambulates, the wrapped materials may loosen and/or shift, which could lead to discomfort and potentially tissue pressures that may not be conducive to healing. Many patients do not feel competent to effectively re-wrap the foot and thus face the options of either living with the compromised wrap or contending with the inconvenience of seeking medical assistance.

Still further, with the patient's foot wrapped, access to the sites at which the pins and/or cables penetrate the soft tissue is obstructed. These sites are prone to infection without proper treatment, that is commonly neglected.

The above-described wraps also act as insulators, thereby maintaining elevated body temperatures that can be detrimental to healing. Whereas it might be optimal to lower the tissue temperature, this is often impractical through the cloth layers of the wrap. A patient's alternative is to remove the wrap, apply a cooling pack, and thereafter replace the wrap. Even if this inconvenience is contended with, the resulting cooling becomes very limited in terms of its duration and effect.

A still further problem is that the wraps do not lend themselves to re-use. Each time the wrap is removed, it is most practical to effect replacement thereof. Aside from the fact that it is necessary to keep on hand significant supplies of the wrapping material, it is also difficult for a patient to effectively re-wrap the leg without assistance.

Still further, the wrap, aside from its detrimental insulating qualities, generally is applied so that it creates a relatively sealed environment over the soft tissue. By reason of there being no, or limited, ventilation, perspiration may cause a sustained accumulation of moisture that could inhibit healing and potentially lead to fungal generation.

Because of the many problems, noted above, patients that have an external fixation assembly applied have generally avoided ambulation. This has lead to lengthened recovery time, poorer patient morale, and oft times to other complications associated with inactivity.

SUMMARY OF THE INVENTION

The invention is directed to a method of preparing a patient's one leg, that is in need of treatment, for ambulation. The method includes the steps of: applying an external fixation assembly, with at least one external frame component, by pinning the at least one external frame component to at least one of the patient's bones in the patient's one leg so as to prepare the patient's one leg for healing; providing a foot assembly having a sole assembly defining a bearing surface and a connecting assembly; and operatively joining the foot assembly to the patient's one leg whereby the patient can walk in a manner whereupon weight of the patient's body is applied by a patient's one foot, that is part of the user's one leg, to the sole assembly and therethrough to and against an underlying surface during ambulation. The foot assembly is constructed so that the connecting assembly: a) maintains the foot assembly operatively joined to the patient's one leg; and b) strategically applies pressure to the patient's one foot on the patient's one leg, thereby to orient the foot in a predetermined manner to permit predictable body weight application to the sole assembly during ambulation in a manner that generated body weight forces during ambulation do not either: i) inhibit healing of the patient's one leg; or ii) disengage or cause a detrimental change of alignment of the external fixation assembly.

In one form, the step of providing a foot assembly involves providing a foot assembly with a connecting assembly that has a bladder assembly with a bladder surface that conformingly engages soft tissue on the patient's one foot and through which pressure is applied to the patient's one foot with the foot assembly operatively joined to the patient's one leg.

In one form, the method further includes the step of controlling a magnitude of the pressure that is applied through the bladder surface to the patient's one foot.

In one form, the step of controlling a magnitude of the pressure involves setting a predetermined magnitude of the pressure that is applied through the bladder within a range of permissible magnitudes.

In one form, the connecting assembly has a surface that engages soft tissue on the patient's one foot and the method further includes the step of changing a temperature of the surface that engages the soft tissue to thereby thermally treat the soft tissue on the patient's one foot.

In one form, the step of providing a foot assembly involves providing a foot assembly with a connecting assembly that has a receptacle with a first substance therein and the step of changing the temperature of the surface that engages the soft tissue involves causing the first substance to cause heat transfer between the first substance and the surface that engages the soft tissue.

In one form, the first substance in the receptacle is in flowable form and the method further includes the step of removing the first substance from the receptacle and placing a second substance that is within a desired temperature range into the receptacle so that heat is conducted between the second substance and the surface that engages the soft tissue to thereby change the temperature of the surface that engages the soft tissue.

In one form, the external fixation assembly additionally has at least one pin and/or cable through which the at least one frame component is pinned to the patient's one leg and the step of providing a foot assembly involves providing a foot assembly having a connecting assembly that defines a receiver through which the at least one pin/cable is directed.

In one form, the step of providing a foot assembly involves providing a foot assembly with a sole assembly that has a bearing surface with a shape that causes body weight forces generated during ambulation to be directed away from a knee on the patient's one leg.

In one form, the step of providing a foot assembly involves providing a foot assembly having a connecting assembly with a fore section and an aft/heel section and the method further includes the step of selecting and maintaining a desired relationship between the fore and aft/heel sections within a range of permissible relationships between the fore and aft/heel sections.

In one form, the step of providing a foot assembly involves providing a foot assembly having a connecting assembly with a reconfigurable strap assembly, and the method further includes the step of reconfiguring the strap assembly to change a pressure applied by the foot assembly to soft tissue on the patient's one foot.

In one form, the method further includes the step of connecting the foot assembly to the fixation assembly.

In one form, the step of connecting the foot assembly to the fixation assembly involves connecting the foot assembly to the fixation assembly so that forces are elastically transmitted between the foot assembly and fixation assembly.

In one form, the step of providing a foot assembly involves providing a foot assembly having a connecting assembly with first and second parts that are joinable in different manners to vary pressure applied by the connecting assembly to soft tissue on the patient's one foot.

In one form, the step of providing a foot assembly involves providing a foot assembly having a connecting assembly with a fore section and an aft/heel section. At least one of the fore and aft/heel sections has first and second parts that are joinable in different manners to vary pressure applied by the connecting assembly to soft tissue on the patient's one foot.

In one form, the step of providing a foot assembly involves providing a foot assembly having a connecting assembly with fore and aft/heel sections that are joined to each other through an elastic joining assembly so that the fore and aft/heel sections can be moved towards and away from each other.

In one form, the step of providing a foot assembly involves providing a foot assembly having a sole assembly with a bearing surface that is textured to avoid slippage relative to a surface against which the bearing surface is placed.

In one form, the step of providing a foot assembly involves providing a foot assembly having a connecting assembly with a fore section and an aft/heel section, wherein the fore section has at least one discrete ventilation opening through which the patient's one foot is exposed.

In one form, the step of providing a foot assembly involves providing a foot assembly having a first strap assembly connected to the sole assembly and the method further includes the step of connecting the first strap assembly to the fixation device.

In one form, the step of providing a foot assembly involves providing a foot assembly having a first strap assembly connected to the sole assembly and the method further includes the step of connecting the first strap assembly to the at least one external frame component.

In one form, the step of providing a foot assembly involves providing a foot assembly having a second strap assembly and the method further includes the step of connecting the second strap assembly to the fixation assembly.

In one form, the step of providing a foot assembly involves providing a foot assembly defining a connecting assembly incorporating an antimicrobial substance that contacts the patient's soft tissue around where the at least one pin and/or cable penetrates the patient's soft tissue.

In one form, the method further includes the step of placing a sheath around the foot assembly to strategically block the foot assembly against exposure to environmental moisture.

In one form, the step of providing a foot assembly involves providing a foot assembly with a sole assembly and connecting assembly that are constructed in a manner and of materials that permit the foot assembly to be exposed to moisture without retaining moisture that is detrimental to healing of the patient's one leg.

DETAILED DESCRIPTION OF THE DRAWINGS

The invention is directed to a method of preparing a patient's leg, that is in need of treatment, for ambulation. For purposes of simplicity herein, the reference throughout to "leg" is intended to include the patient's foot.

Figure 1:
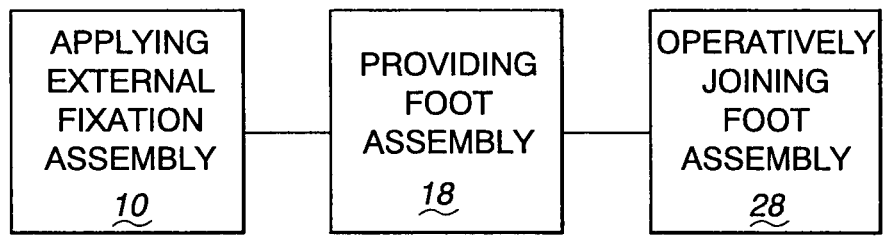
FIG. 1 is a block diagram representation of one method of preparing a patient's leg, that is in need of treatment, for ambulation, according to the present invention, and utilizing an external fixation assembly and a foot assembly.

As shown in FIG. 1, the method includes the step of applying an external fixation assembly to at least one of the patient's bones in the patient's one leg so as to prepare the patient's one leg for healing. This step is shown in schematic form in FIG. 1 at block 10. The external fixation assembly, as shown in generic form at 12 in FIG. 2, consists of at least one external frame component 14 that is pinned to at least one of the patient's bones in the patient's one leg through at least one pin/cable 16.

Figure 3:
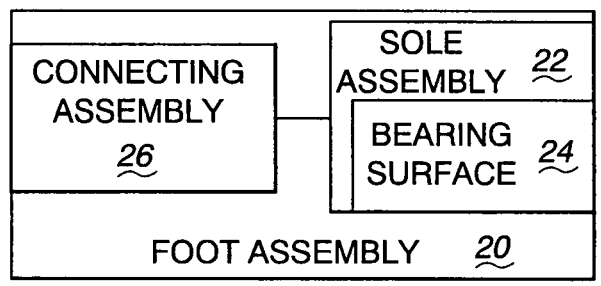
FIG. 3 is a schematic representation of the foot assembly used in the method of FIG. 1.

As shown at block 18 in FIG. 1, the method further contemplates that a foot assembly is provided of the type shown generically in FIG. 3 at 20. The foot assembly 20 consists of a sole assembly 22, defining a bearing surface 24, and a connecting assembly 26.

As shown at block 28 in FIG. 1, the method further includes the step of operatively joining the foot assembly 20 to the patient's one leg, whereby the patient can walk in a manner whereupon weight of the patient's body is applied by a patient's one foot, that is part of the users one leg, to the sole assembly 22 to and against an underlying surface during ambulation.

The foot assembly 20 is constructed to: a) maintain the foot assembly 20 operatively joined to the patient's one leg; and b) strategically apply pressure to the patient's one foot on the patient's one leg, thereby to orient the foot in a predetermined manner to permit predictable body weight application to the sole assembly 22 during ambulation. This is done in a manner so that generated body weight forces do not either: i) inhibit healing of the patient's one leg; or ii) disengage or cause a detrimental change of alignment of the external fixation assembly 12.

Figure 2:
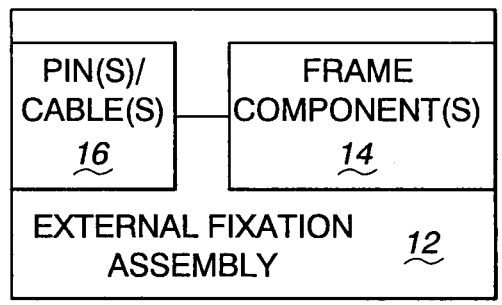
FIG. 2 is a schematic representation of the external fixation assembly used in the method of FIG. 1.

The method and structure are shown in FIGS. 1 and 2 in schematic form in that the invention contemplates virtually a limitless number of different variations of both the method and apparatus as depicted and described in only exemplary forms herein. This generic disclosure is intended to encompass variations beyond those exemplary forms.

Figure 4:
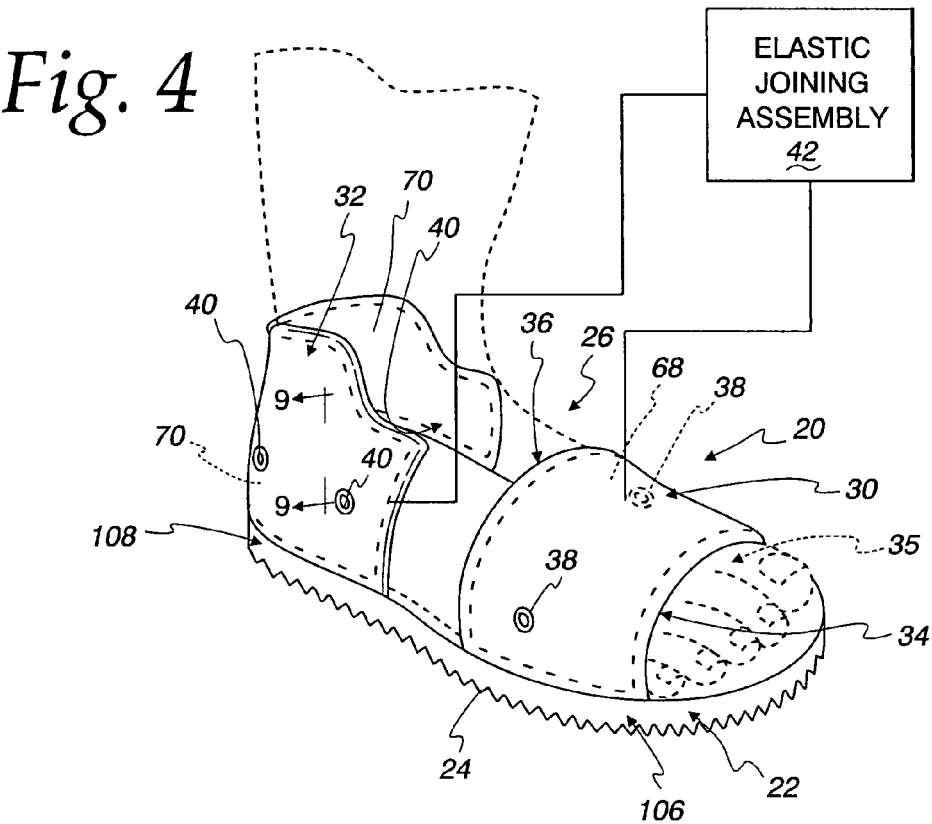
FIG. 4 is a perspective view of one form of the foot assembly in FIG. 3 operatively joined to a patient's leg, with the foot assembly consisting of a sole assembly and a connecting assembly.

In FIG. 4, one form of the foot assembly 20 is shown with the sole assembly 22 and the connecting assembly 26. The sole assembly 22 has a bearing surface 24 that is textured to avoid slippage relative to a surface against which the bearing surface 21 is placed. The sole assembly 22 is preferably made of a relatively hard, or stiff, material that will maintain shape generally but have sufficient resiliency to compress or reshape under the patient's weight during ambulation and absorb impact forces to a certain degree.

The connecting assembly 26, atop the sole assembly 22, is made up of a fore section 30 and an aft/heel section 32. In this embodiment, the fore section 30 has a discrete, ventilation opening 34 through which a patient's foot 35, at the toe region, is exposed. A separate ventilation opening 36 is provided between the fore and aft/heel sections 30, 32. The fore and/or aft heel sections 30, 32 are preferably made from a "breathable" material.

The fore section 30 has pre-formed receivers 38 for the pin(s)/cable(s) 16. Like receivers 40 are provided on the aft/heel section 32.

Optionally, the fore and aft/heel sections 30, 32 are joined to each other through an elastic joining assembly 42 so that the fore and aft/heel sections 30, 32 can be moved towards and away from each other. It is also understood that the fore and aft/heel sections 30, 32 could be directly connected to each other above the sole assembly 22, as by one continuous piece of material or fixedly joined pieces of material. More preferably, however, distinct and relatively movable sections are incorporated into the construction.

Figure 5:
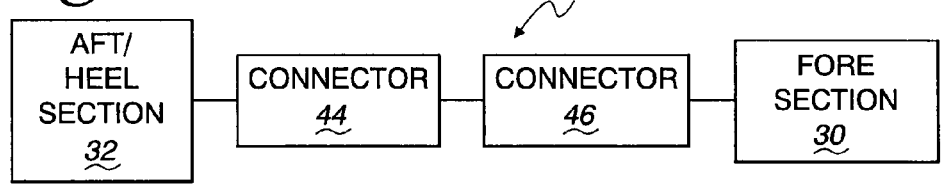
FIG. 5 is a schematic representation of a joining assembly between fore and aft/heel sections on the connecting assembly on the foot assembly in FIG. 4.

In one form, shown in FIG. 5, a joining assembly 42' consists of a connector 44 on the aft/heel section 32 and a connector 46 on the fore section 30, with the connectors 44, 46 designed to cooperate with each other to maintain a selected, desired, relationship between the fore and aft/heel sections 30, 32. These connectors 44, 46 may facilitate adjustable connection whereby a desired relationship between the fore and aft/heel sections 30, 32 can be selected and maintained within a range of permissible relationships therebetween. The connectors 44, 46 may be in the form of straps with adjustable lengths, straps that can be joined to produce different effective lengths through the use of cooperating hook and loop type fasteners, or other cooperating structures, known to those in this art, that will achieve the above end. The effective length defined jointly by the connectors 44, 46 may be variably fixed or elastic in nature.

Figure 6:
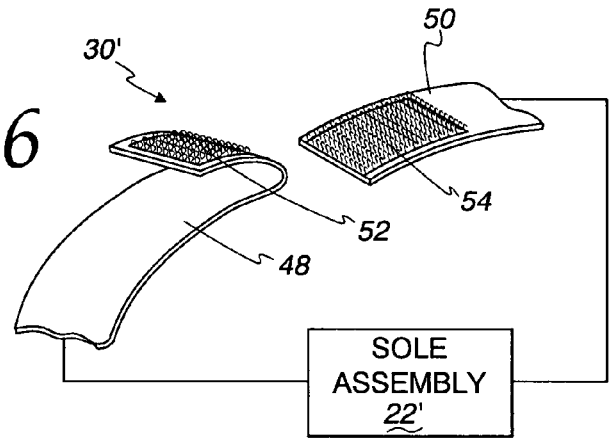
FIG. 6 is a partially schematic representation of a modified form of the fore section of the connecting assembly as shown in FIG. 4.

One modification contemplated, from the basic construction shown in FIG. 3, is to the fore section 30', as shown in FIG. 6. Rather than having the fore section 30 formed as in FIG. 4 with one piece bridging the sides of the sole assembly 22, in FIG. 6, the fore section 30' incorporates first and second parts 48, 50, as shown in the form of straps on a sole assembly 22'. Cooperating connecting components 52, 54 thereon allow the first and second parts 48, 50 to be releaseably joined in different manners to vary pressure applied by the fore section 30' to soft tissue on the patient's foot. In this embodiment, the components 52, 54 are shown as cooperating hook and loop type components, of well known construction. Alternatively, cooperating snap components, buttons, or any other structure known to those skilled in the art, might be utilized to facilitate pressure adjustment through the fore section 30.

It should be further understood that the parts 48, 50 may make up the entire fore section 30' or may overlie another component and thereby draw that other component into tighter engagement with the soft tissue thereunder.

Figure 7:
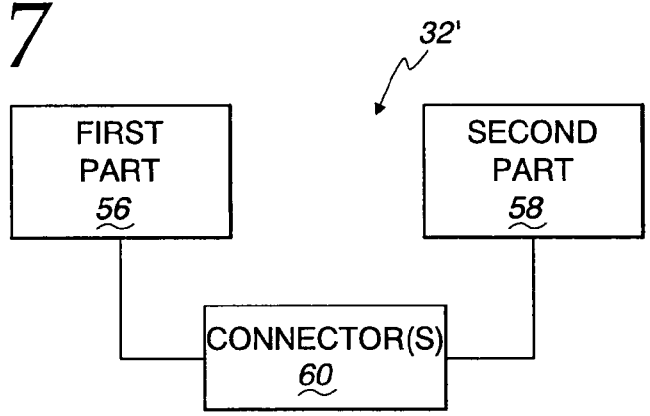
FIG. 7 is a schematic representation of a modified form of the aft/heel section of the connecting assembly in FIG. 4.

A similar construction can be provided for the aft/heel section 32, modified as shown at 32' in FIG. 7. The aft/heel section 32' may include first and second parts 56, 58 that are joinable through a connector or connectors 60 to vary pressure applied to soft tissue on the patient's foot towards the heel region thereof and/or strategically change the contour of the aft/heel section 32'. In the latter case, the heel curvature might be changed to comfortably accommodate different foot sites and conditions. As with the fore section 30', the first and second parts 56, 58 on the aft/heel section 32' may define substantially the entirety of the aft/heel section 32 or may be disposed over another component or components to draw that component(s) with a variable pressure against the soft tissue at the heel region.

One or both of the fore and aft/heel sections 30', 32' may be incorporated and are desirable from the standpoint that they permit conformity to different foot sizes and controlled pressure application that may minimize swelling and pain, thereby affording the most comfort to the user when at rest and during ambulation. Circulation may be optimized through these pressure adjustments.

The connecting parts may be strap components or entire walls that are connectable in different relationships with each other at the fore and/or aft/heel sections 30', 32'.

Figure 8:
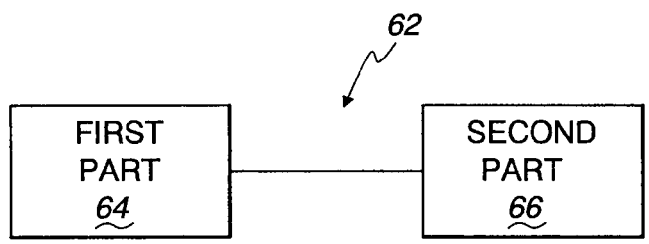
FIG. 8 is a schematic representation of a reconfigurable strap assembly, consisting of first and second parts, that can be joined to vary pressure applied through the foot assembly on a user's soft tissue.

As an alternative to the above constructions and/or in addition thereto, the foot assembly 20 may incorporate at any strategic location a reconfigurable strap assembly, as shown at 62 in FIG. 8. The strap assembly 62 consists of first and second parts 64, 66 that can be joined in different manners to change an effective length for the strap assembly 62, thereby to change a pressure applied by the foot assembly 20 to soft tissue at locations at which the strap assembly 62 is incorporated. The first and second parts 64, 66 may be strap lengths that are joinable through any conventional means. Alternatively, one may be a strap and the other a buckle, or other holding mechanism. The length may be shortened for shape variation and increased pressure application at any region of the user's foot for purposes of comfort, support, maximized circulation, and control of swelling. This discrete strap construction facilitates particularly connection around the components making up the external fixation assembly 12.

Figure 9:
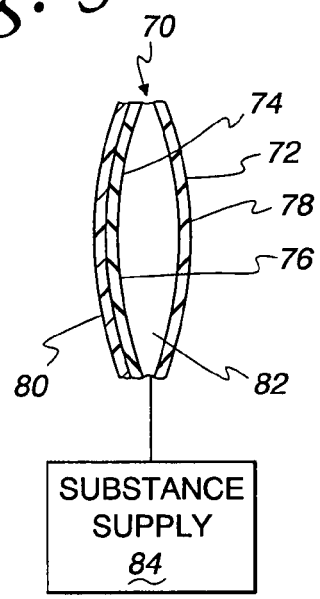
FIG. 9 is a cross-sectional view of the aft/heel section taken along line 9-9 of FIG. 1 and showing a bladder with a flowable substance therein.

To add an additional dimension to the user's comfort and also to control pressure application for purposes of support and healing, at least one bladder assembly may be incorporated. In FIG. 4, separate bladder assemblies 68, 70 are incorporated into the fore section 30 and aft/heel section 32, respectively. As shown additionally in FIG. 9, the exemplary bladder assembly 70 may consist of inner and outer walls 72, 74, with a receptacle 76 defined therebetween.

The inner wall 72 has a surface 78 that may directly or indirectly bear against the soft tissue on the user's foot 35. The outer wall 74 may likewise define the exposed surface of the aft/heel section 32. However, in this embodiment, a separate, outer, exposed wall 80 is provided against which the outer wall 74 of the bladder assembly 70 is placed and by which it is reinforced. The wall 80 may have a pre-defined shape or at least a relatively rigid construction to reinforce the bladder assembly 70. By increasing pressure in the receptacle 76, the bladder surface 78 is caused to conformingly engage soft tissue on the patient's foot 35.

In one form, the receptacle 76 is filled with air or another flowable substance 82. A predetermined amount of the substance 82 may be captured within the receptacle 76. With the user's foot 35 squeezed into the aft/heel section 32, the surface 78 is caused to conform around the heel portion of the user's foot 25 to afford the above-noted advantages. The bladder walls 72, 74 may be made from a plastic or rubber material of a type that can be selected by one skilled in the art based upon the degree of conformity desired and pressure accommodating ability that is necessary.

Optionally, the bladder assembly 70 might be equipped to communicate with a substance supply 84 (FIG. 9), whereby the magnitude of the pressure of the substance 82 within the receptacle 76 can be controlled to set a predetermined magnitude of pressure within a permissible range of magnitudes, as opposed to having a fixed pressure that results in the absence of this feature.

Figure 10:
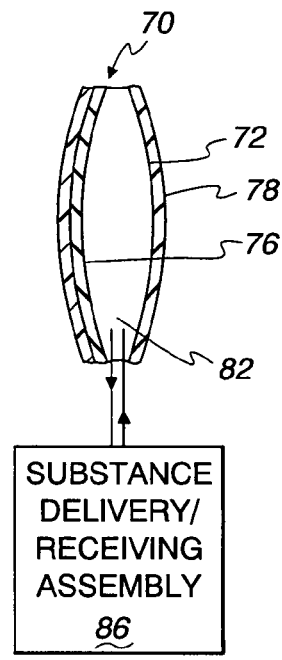
FIG. 10 is a view as in FIG. 9 wherein a substance delivery/receiving assembly is provided to direct a substance into and from the receptacle.

As shown in FIG. 10, the bladder assembly 70 may be equipped with a substance delivery/receiving assembly 86 that allows circulation of substance into and out of the receptacle 76, thereby allowing change in the magnitude of pressure therewithin.

Additionally, the structure in FIG. 10 facilitates changing of the temperature of the substance 82. Through heat conduction through the wall 72, the temperature of the surface 78 can be changed as desired to thermally treat the soft tissue on the patient's foot 35 in contact with the surface 78. For example, a separate cold liquid substance 82, of the same or different composition, might be newly introduced and continuously circulated or delivered without immediate recovery.

Like heat transfer can be effected using a warmer substance or one at any temperature as desired to meet the particular objective. Regardless of whether the heat transfer effects heating or cooling of the soft tissue, the flowable substance 82 may be permanently placed in the receptacle 76, temporarily placed therein, or continuously recirculated thereinto and therefrom.

The bladder assembly 68 may perform in like fashion. Like bladder assemblies may be placed elsewhere at discrete locations or over a majority, or the entirety, of the areas of the surfaces that engage the user's soft tissue at the fore section 30 and/or aft/heel section 32.

Figure 11:
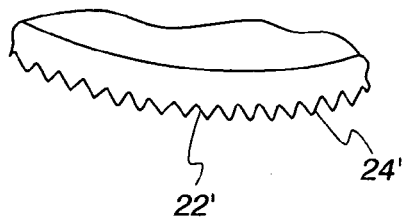
FIG. 11 is a fragmentary, elevation view of a modified form of sole assembly on the foot assembly.

To add additional comfort to the patient and potentially to control the direction/path of transmission of forces during walking strategically through the user's leg, a sole assembly 22', as shown in FIG. 11, may have a bottom surface 24' that is contoured over a substantial portion of its area. In this embodiment, the bearing surface 24' on the sole assembly 22' has a curved shape that can be placed to cause body weight forces generated during ambulation to be directed away from a knee on the patient's leg. In the depicted embodiment, the curved bottom surface 24' causes a rocking action during each step that can be controlled to direct forces away from the knee region. Other shapes can be integrated to direct these forces in a desired manner, thereby to facilitate the healing process and avoid application of detrimental forces during ambulation.

Figure 12:
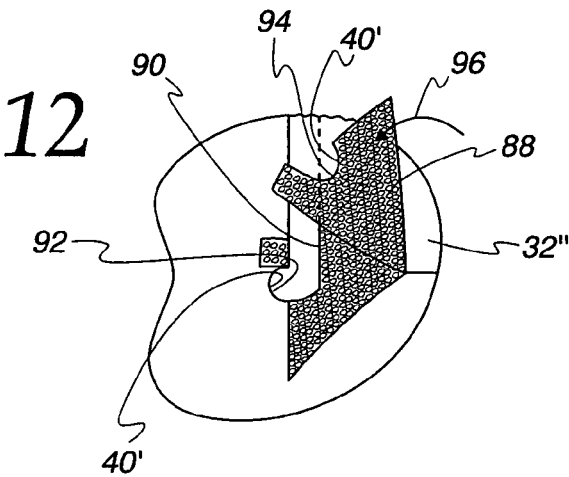
FIG. 12 is an enlarged, fragmentary, elevation view of a part of a modified form of foot assembly wherein a receiver for a pin/cable on the external fixation assembly can be selectively opened and closed to facilitate joining and separation of the foot assembly.

Another optional feature is the incorporation of structure, shown in FIG. 12, on a corresponding aft/heel section 32", that allows opening of the receivers 40' for pins/cables 16, as to facilitate placement and removal of the foot assembly 20. This is desirable particularly when dressings are required to be changed on a regular basis. More specifically, a flap 88 is bendable to the position shown to expose a feeder slot 90 in communication with a receiver portion 92. A cooperating receiver portion 94 is provided on the flap 88. With the flap 88 folded downwardly as indicated by the arrow 96, the receiver portions 92, 94 cooperatively continuously extend around a pin/cable 16 extending therethrough. By bending the flap 88 upwardly to the position shown, the feeder slot 90 is exposed, thereby allowing the pin/cable 16 to be translated lengthwise therethrough to allow separation of the foot assembly 20 from the external fixation assembly 12. A similar arrangement can be provided at each location wherein a pin/cable 16 is directed through the foot assembly 20.

Figure 13:
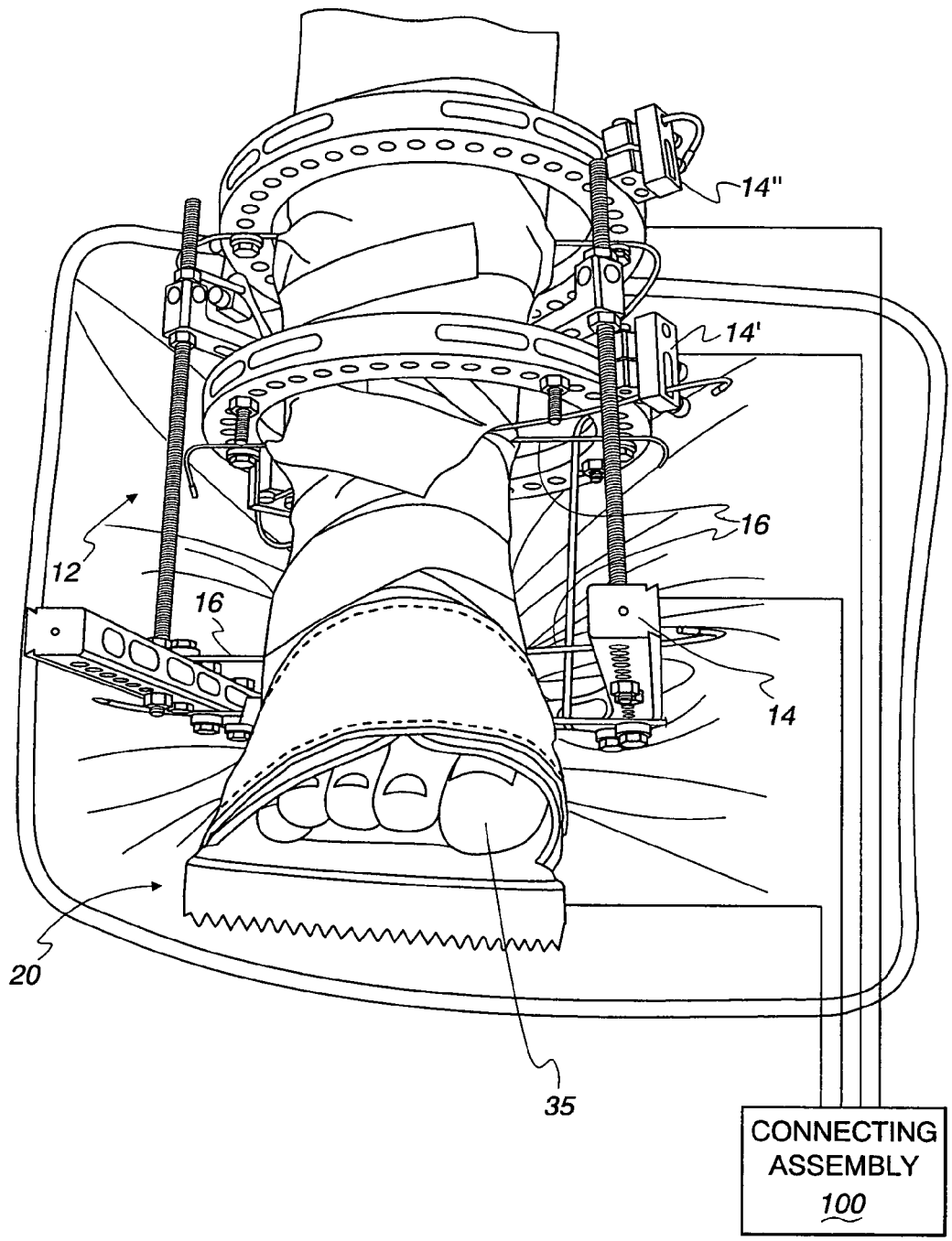
FIG. 13 is a perspective view of one form of external fixation device pinned to a patient's leg and with the inventive foot assembly operatively joined to the patient's leg.

For purposes of stabilizing the patient's foot 35, the foot assembly 20 can be connected to the external fixation assembly 12, as shown in one specific form in FIG. 13. As shown in FIG. 13, a connecting assembly 100 connects between the foot assembly 20 and any one of three depicted frame components 14, 14', 14" making up the external fixation assembly 12. The connecting assembly 100 preferably elastically transmits forces between the foot assembly 20 and external fixation assembly 12, though this is not a requirement.

Figure 14:
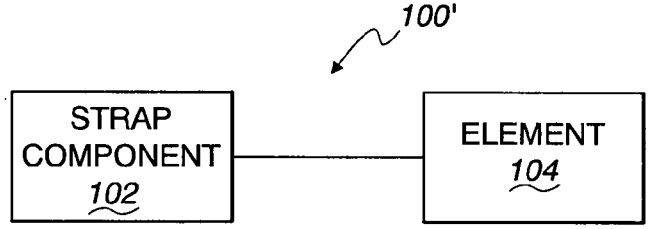
FIG. 14 is a schematic representation of a connecting assembly between the external fixation device and foot assembly.

In one exemplary form shown in FIG. 14, the connecting assembly 100' is in the form of a strap assembly with a strap component 102 connected to another element 104 that may be another length of strap or a suitable connection such as a buckle, snap, etc. The strap component 102 may be of a substantially fixed length or elastic.

Each connecting assembly 100/100' may join between any part of the external fixation assembly 12, and preferably at least one of the frame components 14, 14', 14" thereon, and the foot assembly 20, at any of a number of different locations. This connection may occur, for example, at the sole assembly 22 as shown at exemplary fore and aft locations 106, 108 (FIG. 3). Multiple connections can be established between the foot assembly 20 and external fixation assembly 12. As just one example, one strap assembly 100' may be connected to the sole assembly 20 and the external fixation assembly 12 at the fore location 106, with a separate strap assembly similarly connecting between the external fixation assembly 12 and the aft location 108.

Figure 15:
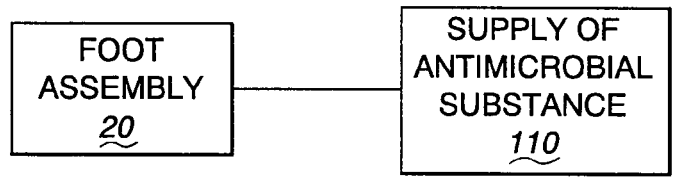
FIG. 15 is a schematic representation of the foot assembly, according to the invention, and incorporating a supply of antimicrobial substance.

To avoid infection of the tissue where the pins/cables 16 penetrate, the foot assembly 20 may incorporate a supply of antimicrobial substance 110, as shown in FIG. 15. The supply 110 may be incorporated in a disc-shaped receptacle around the various receivers 38, 40 in a manner whereby the antimicrobial substance contacts the penetrating pin/cable 16 and the patient's soft tissue around where the pin/cable 16 enters the soft tissue.

To avoid complications induced by exposure to moisture, as through environmental conditions or when bathing, the sole assembly 22 and connecting assembly 26 may be constructed in a manner and from materials that permit the entire foot assembly 20 to be exposed to moisture without retaining moisture that is detrimental to the healing of the patient's leg. Materials of construction and venting are selected and incorporated to achieve this end. The entire foot assembly 20 may be made from materials that allow it to be washed for re-use by the same patient and potentially sterilized for use by multiple patients.

Figure 16:
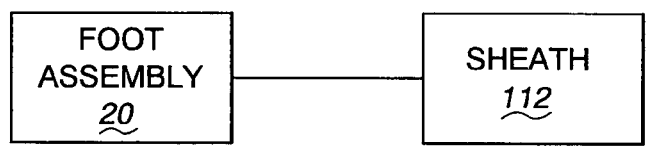
FIG. 16 is a schematic representation of the inventive foot assembly with a protective sheath to control exposure of the foot assembly to moisture.

Alternatively, as shown in FIG. 16, a sheath 112 can be provided in combination with the foot assembly 20 to strategically block the foot assembly against exposure to environmental moisture. The sheath 112 may be integrally formed with a foot assembly 20 and changeable between sealing and exposed states. Alternatively, the sheath 112 may be a separate element that is connected to accomplish the above objective. This arrangement potentially facilitates bathing through use of a bath or shower without requiring removal of the foot assembly 20.

The foregoing disclosure of specific embodiments is intended to be illustrative of the broad concepts comprehended by the invention.

The invention claimed is:

1. A method of preparing a patient's one leg, that is in need of treatment, for ambulation, the method comprising the steps of:
    applying an external fixation assembly comprising at least one external frame component by pinning the at least one external frame component to at least one of the patient's bones in the patient's one leg so as to prepare the patient's one leg for healing;
    providing a foot assembly comprising a sole assembly for engaging a bottom area of a foot on the patient's one leg and defining a bearing surface with an area to underlie substantially all of the bottom area of the foot and a connecting assembly, the sole assembly made of a material that will maintain shape generally but have sufficient resiliency to compress or re-shape under the patient's weight; and
    after applying the external fixation assembly so that the patient's one leg is prepared for healing, operatively joining the foot assembly to the patient's one leg whereby the patient can walk in a manner whereupon weight of the patient's body is applied by a patient's one foot, that is part of the user's one leg, to the sole assembly and therethrough to and against an underlying surface during ambulation,
    whereby the step of providing a foot assembly comprises providing a foot assembly with a connecting assembly that: a) maintains the foot assembly operatively joined to the patient's one leg; and b) strategically applies pressure to the patient's one foot on the patient's one leg thereby to orient the foot in a predetermined manner to permit predictable body weight application to the sole assembly during ambulation in a manner that body weight forces generated during ambulation do not either: i) inhibit healing of the patient's one leg; or ii) disengage or cause a detrimental change of alignment of the external fixation assembly.

2. The method of preparing a patient's one leg according to claim 1 wherein the step of providing a foot assembly comprises providing a foot assembly with a connecting assembly that comprises a bladder assembly with a bladder surface that conformingly engages soft tissue on the patient's one foot and through which pressure is applied to the patient's one foot with the foot assembly operatively joined to the patient's one leg.

3. The method of preparing a patient's one leg according to claim 2 further comprising the step of controlling a magnitude of the pressure that is applied through the bladder surface to the patient's one foot.

4. The method of preparing a patient's one leg according to claim 3 wherein the step of controlling a magnitude of the pressure comprises setting a predetermined magnitude of the pressure that is applied through the bladder within a range of permissible magnitudes.

5. The method of preparing a patient's one leg according to claim 1 wherein the connecting assembly comprises a surface that engages soft tissue on the patient's one foot and further comprising the step of changing a temperature of the surface that engages the soft tissue to thereby thermally treat the soft tissue on the patient's one foot.

6. The method of preparing a patient's one leg according to claim 5 wherein the step of providing a foot assembly comprises providing a foot assembly with a connecting assembly that comprises a receptacle with a first substance therein and the step of changing the temperature of the surface that engages the soft tissue comprises causing the first substance to cause heat transfer between the first substance and the surface that engages the soft tissue.

7. The method of preparing a patient's one leg according to claim 6 wherein the first substance in the receptacle is in flowable form and further comprising the step of removing the first substance from the receptacle and placing a second substance that is within a desired temperature range into the receptacle so that heat is conducted between the second substance and the surface that engages the soft tissue to thereby change the temperature of the surface that engages the soft tissue.

8. The method of preparing a patient's one leg according to claim 1 wherein the external fixation assembly additionally comprises at least one pin and/or cable through which the at least one frame component is pinned to the patient's one leg and the step of providing a foot assembly comprises providing a foot assembly comprising a connecting assembly that defines a receiver through which the at least one pin/cable is directed.

9. The method of preparing a patient's one leg according to claim 8 wherein the step of providing a foot assembly comprises providing a foot assembly defining a connecting assembly incorporating an antimicrobial substance that contacts the patient's soft tissue around where the at least one pin and/or cable penetrates the patient's soft tissue.

10. The method of preparing a patient's one leg according to claim 1 wherein the steps of providing a foot assembly comprises providing a foot assembly with a sole assembly that has a bearing surface with a shape that causes body weight forces generated during ambulation to be directed away from a knee on the patient's one leg.

11. The method of preparing a patient's one leg according to claim 1 wherein the step of providing a foot assembly comprises providing a foot assembly comprising a connecting assembly with a fore section and an aft/heel section with each of the fore and aft/heel sections engaging the patient's one foot and further comprising the step of selecting and maintaining a desired relationship between the fore and aft/heel sections within a range of permissible relationships between the fore and aft/heel sections.

12. The method of preparing a patient's one leg according to claim 1 wherein the step of providing a foot assembly comprises providing a foot assembly comprising a connecting assembly with a strap assembly with at least one flexible strap component that is reconfigurable, and further comprising the step of reconfiguring the flexible strap component on the strap assembly to thereby change a pressure applied by the foot assembly to soft tissue on the patient's one foot.

13. The method of preparing a patient's one leg according to claim 1 further comprising the step of connecting the foot assembly to the fixation assembly.

14. The method of preparing a patient's one leg according to claim 13 wherein the step of providing a foot assembly comprises providing a foot assembly comprising a first strap assembly with a reconfigurable flexible strap connected to the sole assembly and further comprising the step of connecting the first strap assembly to the fixation device.

15. The method of preparing a patient's one leg according to claim 14 wherein the step of providing a foot assembly comprises providing a foot assembly comprising a second strap assembly and further comprising the step of connecting the second strap assembly to the fixation assembly.

16. The method of preparing a patient's one leg according to claim 13 wherein the step of connecting the foot assembly to the fixation assembly comprises connecting the foot assembly to the fixation assembly so that forces are elastically transmitted between the foot assembly and fixation assembly.

17. The method of preparing a patient's one leg according to claim 13 wherein the step of providing a foot assembly comprises providing a foot assembly comprising a first strap assembly with a reconfigurable flexible strap connected to the sole assembly and further comprising the step of connecting the first strap assembly to the at least one external frame component using the reconfigurable flexible strap.

18. The method of preparing a patient's one leg according to claim 1 wherein the step of providing a foot assembly comprises providing a foot assembly comprising a connecting assembly with first and second parts that are joinable in different manners to vary pressure applied by the connecting assembly to soft tissue on the patient's one foot.

19. The method of preparing a patient's one leg according to claim 1 wherein the step of providing a foot assembly comprises providing a foot assembly comprising a connecting assembly with a fore section and an aft/heel section with each of the fore and aft/heel sections engaging the patient's one foot, at least one of the fore and aft/heel sections having first and second parts that are joinable in different manners to vary pressure applied by the connecting assembly to soft tissue on the patient's one foot.

20. The method of preparing a patient's one leg according to claim 1 wherein the step of providing a foot assembly comprises providing a foot assembly comprising a connecting assembly with fore and aft/heel sections that are joined to each other through an elastic joining assembly so that the fore and aft/heel sections can be moved towards and away from each other.

21. The method of preparing a patient's one leg according to claim 1 wherein the step of providing a foot assembly comprises providing a foot assembly comprising a sole assembly with a bearing surface that is textured to avoid slippage relative to a surface against which the bearing surface is placed.

22. The method of preparing a patient's one leg according to claim 1 wherein the step of providing a foot assembly comprises providing a foot assembly comprising a connecting assembly with a fore section and an aft/heel section wherein the fore section has at least one discrete ventilation opening through which the patient's one foot is exposed.

23. The method of preparing a patient's one leg according to claim 1 further comprising the step of placing a sheath around the foot assembly to strategically block the foot assembly against exposure to environmental moisture.

24. The method of preparing a patient's one leg according to claim 1 wherein the step of providing a foot assembly comprises providing a foot assembly with a sole assembly and connecting assembly that are constructed in a manner and of materials that permit the foot assembly to be exposed to moisture without retaining moisture that is detrimental to healing of the patient's one leg.

\* \* \* \* \*